United States Patent
Chubachi et al.

[11] Patent Number: 5,840,028
[45] Date of Patent: Nov. 24, 1998

[54] ULTRASONIC DIAGNOSTIC EQUIPMENT

[75] Inventors: Noriyoshi Chubachi; Hiroshi Kanai; Yoshiro Koiwa, all of Sendai, Japan

[73] Assignee: Japan Science and Technology Corporation, Saitama, Japan

[21] Appl. No.: 786,797

[22] Filed: Jan. 21, 1997

[30] Foreign Application Priority Data

Jun. 24, 1996 [JP] Japan ................................. 8-163418

[51] Int. Cl.⁶ .................................................. A61B 8/00
[52] U.S. Cl. .............................................. 600/437; 600/450
[58] Field of Search .................... 128/660.01, 660.02, 128/661.03–661.04, 661.07–661.1; 600/437, 438, 449–450, 454–457, 402, 300, 305

[56] References Cited

U.S. PATENT DOCUMENTS

| | | | |
|---|---|---|---|
| 4,233,989 | 11/1980 | Larach et al. | 128/661.04 |
| 4,936,308 | 6/1990 | Fukukita et al. | 128/660.02 |
| 4,984,567 | 1/1991 | Kageyama et al. | 128/660.02 |

FOREIGN PATENT DOCUMENTS 62-266040  11/1987  Japan .

Primary Examiner—Francis Jaworski
Attorney, Agent, or Firm—McGlew and Tuttle

[57] ABSTRACT

This invention relates to an ultrasonic diagnostic equipment usable to measure small vibrations in myocardial tissues superimposed on a large amplitude vibration of heartbeat. And it comprises a large amplitude motion analyzing means for deciding the an instantaneous position of the object by using the amplitude and phase of the detected signal and tracking a large amplitude of motion of the object, and a small vibration analyzing means for detecting a small vibration superimposed on the large amplitude motion by analyzing, succeeding positions of the large amplitude motion obtained from the large amplitude motion analyzing means. By using this invention, a local elasticity of width of 1–2 mm in myocardium and arterial wall can be evaluated noninvasively.

10 Claims, 16 Drawing Sheets

WAVEFORMS OF A SIMPLE MODEL OF THE RECEIVED COMPLEX SIGNALS

GRAPHS SHOWING CHANGE OF THE ERROR $\alpha(\Delta\theta(\delta x); \delta x)$

FIG. 4
AN ILLUSTRATION EXPLAINING THEORITICAL LIMITATIONS IN THE ESTIMATION OF THE VELOCITY OF AN OBJECT BY (A) THE PREVIOUS PLL-BASED METHOD AND (B) THE METHOD PROPOSED IN THIS INVENTION
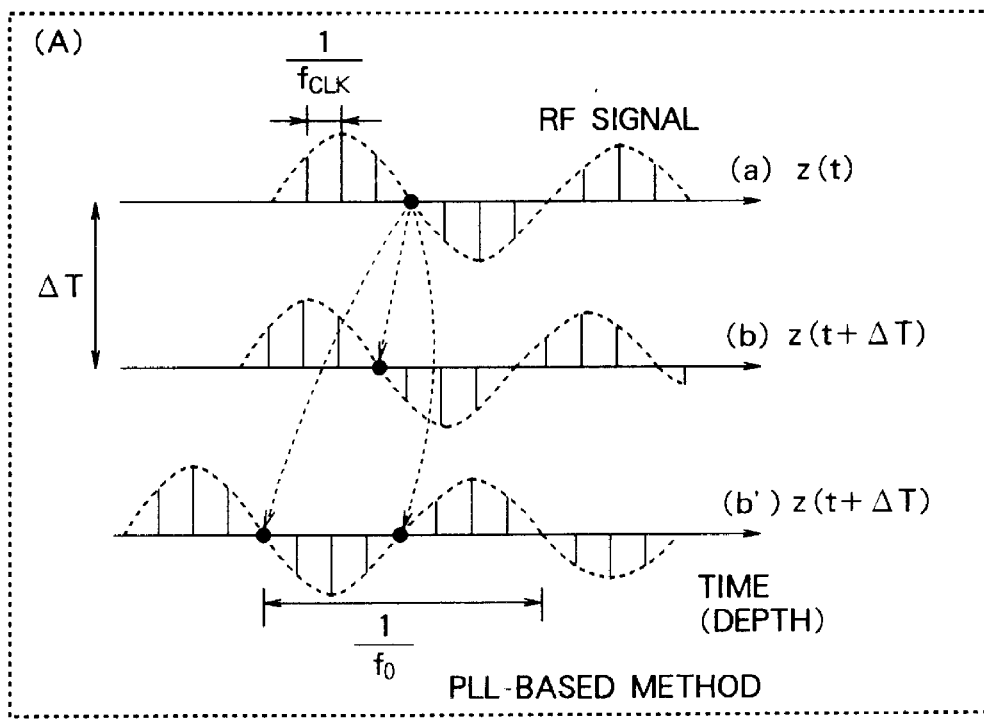
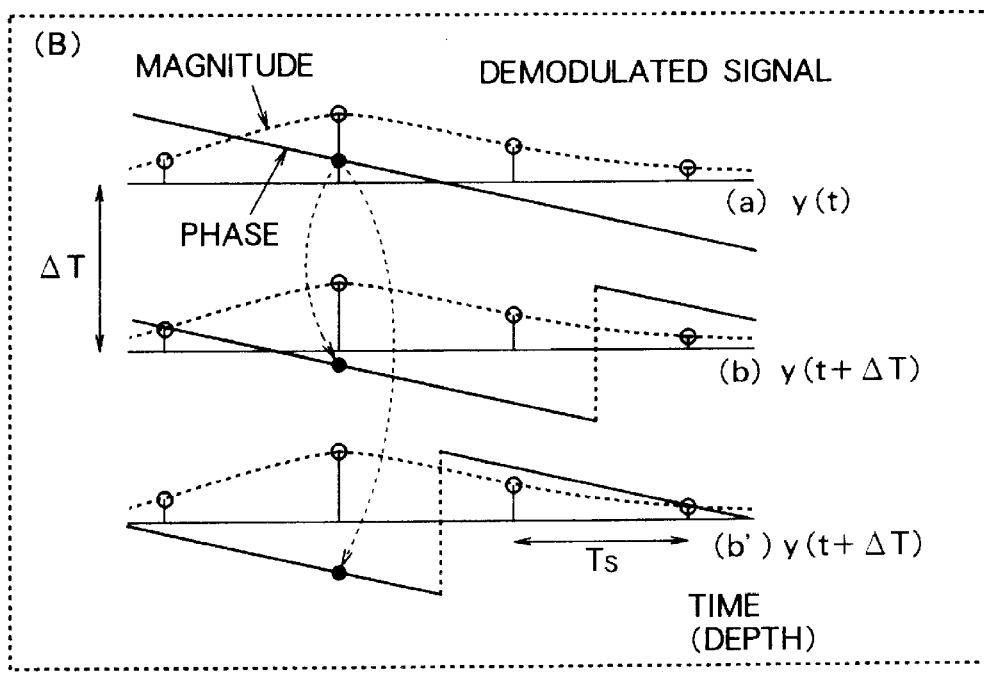

THEORITICAL COMPARISON OF ERROR AND THE LIMITATION IN THE ESTIMATION OF THE VELOCITY OF AN OBJECT BY THE PREVIOUS PLL-BASED METHOD AND THE METHOD PROPOSED IN THIS INVENTION

A STANDARD B-MODE CROSS-SECTIONAL IMAGE

A MAGNIFIED WAVEFORM OF MOVEMENT VELOCITY OF INTERVENTRICULAR SEPTUM

THE WAVEFORMS OF THE VIBRATION SIGNALS ON THE LV SIDE OF THE INTERVENTRICULAR SEPTUM OF HEALTHY SUBJECT (LEFT) AND THEIR POWER SPECTRA (RIGHT)

THE WAVEFORMS OF THE SMALL VIBRATION SIGNALS ON THE LV SIDE OF THE INTERVENTRICULAR SEPTUM FOR PATIENTS WITH MYOCARDIAL DESESE (LEFT) AND THEIR POWER SPECTRUM (RIGHT)

THE WAVEFORM SHOWING THE MOVEMENT VELOCITY OF INTERVENTRICULAR SEPTUM

EXPLANATION DRAWINGS OF CHANGE OF
ARTERIAL WALL THICKNESS BY
A HEARTBEAT MOTION

EXPLANATION DRAWING OF RESULTS OF
INTERVENTRICULAR PRESSURE ESTIMATION

AN EXPLANTION DRAWING OF ERROR OF INTERVENTRICULAR PRESSURE ESTIMATION AT THE MAXIMUM POWER IN END-DIASTLIC PERIOD

ULTRASONIC DIAGNOSTIC EQUIPMENT

BACKGROUND OF THE PRESENT INVENTION

This invention relates to an ultrasonic diagnostic equipment which is possible to measure noninvasively the movement velocity signal of a part of heart, artery and the other organs by using ultrasonic wave, especially relates to an ultrasonic diagnostic equipment usable to measure small vibrations in myocardial tissues superimposed on a large amplitude vibration of heartbeat.

EXPLANATION OF PRIOR ART

The techniques for ultrasonic diagnostic equipment are progressed highly in Japan, and there is not in the world a precedent study on "measurement of a small amplitude vibration of myocardial tissues superimposed on a large amplitude vibration of heartbeat" and the diagnostic equipment using the vibration measuring methods.

On the other hand, the electrocardiogram and the phonocardiogram analysis have their history over a hundred year, and their various measurement methods and analysis have been developed. But they have some problems that (a) only signals of low frequency less than several tens Hz of frequency are contained in detected signals, (b) regional information in a myocardium is not contained and (c) a range possible to obtain signals in one cardiac cycle is restricted.

The other principal prior arts are explained in the following.

Zero Cross Point Detection of RF Signal Method

A measuring method of vibration in heart wall or internal tissues by using ultrasonic pulse transmitted from external of a body has been reported. It measures the displacement of an objects based on the zero cross timing of RF (Radio frequency) signal of the reflected ultrasonic wave from the object. In this method, quantization error depending on the clock frequency $f_{CLK}$ of circuit is caused. The displacement signal is obtained by integrating the velocity signal, therefore the displacement signal can be measured with small error, but when the velocity signal is obtained by differentiation of the displacement, it causes a significant error. Only from a few Hz to ten Hz of frequency components are contained in the displacement signal of heartbeat, therefore the meaning result cannot be obtained from the spectrum analysis of the displacement signal.

Tissue Doppler Method

As a reference on this technique, "Japanese published patent specification, Tokkaisho No. 62-266040" (applicant of Toshiba LTD) is cited. It discloses an ultrasonic diagnostic equipment that receives reflected waves of ultrasonic pulse transmitted to an object and displays its ultrasonic images based on the reflected waves. It comprises a phase detecting means for detecting phase of reflected waves at any time, and sampling point designating means for designating sample points of any positions of reflecting waves, sample shifting means for detecting the phase deference at sampling points of the reflecting waves and shifting the sampling points by the distance accordingly to the phase difference, and dynamic measuring and displaying means for automatically measuring the object movement by tracing the translation of sample points and displaying the movement of the target on a display.

This equipment detects the phase deference of sampling points of the reflected waves, and moves the sample points by the distance depending on the phase deference. On the other hand, the distances of sampling points are several hundreds μm and the invivo wave length of ultrasonic wave of 3.5 MHz is about 500 μm, therefore, if sample points are close, only same signals can be obtained, so it is ineffective to make the distance between succeeding sampling points more close. In either case, as the distance between sample points is several hundreds μm, its accuracy on measuring the displacement is same as this order, therefore the accuracy of the prior art is very rough.

The displacement signals are obtained by integrating velocity signals on the displacement measurement. The displacement signals can be measured by using the prior art, but when they are converted to velocity signals by differentiation, the measuring error becomes large. Only from a few Hz to ten Hz of frequency components are contained in the displacement signal of heartbeat, therefore, the meaning result cannot be obtained from the spectrum analysis of the displacement signal.

Further, the equipment gathers reflected waves obtained from the transmitted ultrasonic pulses of a few or over ten Hz of frequency (let us suppose that it is N), and calculates their average Doppler shift by averaging them. Therefore, the time resolution on the obtained velocity signal is bad and the velocity signal is sampled with sampling frequency of one Nth of pulse transmission frequency PRF.

In the prior art Doppler measurement of blood flow velocity, the distance from a ultrasonic probe to an object reflecting the ultrasonic wave is constant, but, in the case of measurement of heart wall vibrations, a wall position moves more than 10 mm according to the heartbeat motion, therefore the distance from the ultrasonic probe to the object changes largely with time passing. This influences the measurement of the myocardial wall vibrations, and it has been cause of errors.

SUMMARY OF THE PRESENT INVENTION

The present invention resolves the prior art problems by tracking highly accurately the object positions which moves with its vibrations.

This invention is that the ultrasonic diagnostic equipment for measuring the position and movement of an object by transmitting ultrasonic wave into an inner body and detecting reflected ultrasonic wave from the object and analyzing it. And it comprises the following means.

A large amplitude motion analyzing means for deciding an instantaneous position of the object by using the amplitude and phase of the detected signal and tracking a large amplitude of motion of the object, and a small vibration analyzing means for detecting a small vibration superimposed on the large amplitude motion by analyzing succeeding positions of the large amplitude motion obtained from said large amplitude motion analyzing means.

FIG. 1 shows a drawing of principle of the present invention.

In FIG. 1, an ultrasonic transducer 1, a chest wall surface 2, a myocardial wall 3, an amplifier 4, a quadrature demodulator 5, an A/D converter 6, a data analysis processing part 7 are shown.

The transducer 1 is driven by ultrasonic wave pulse of frequency ΔT and transmits ultrasonic pulse for the inner body from the chest wall surface 2. The transmitted ultrasonic wave is reflected from a vibrating heart wall of velocity v(t) and the reflected waves are received by the transducer 1. The ultrasonic signal of the received wave is amplified with the amplifier 4 and detected with the quadrature demodulator 5, and output signals from it are converted to digital data sampled with the sampling frequency of Ts in the A/D converter 6 and they are input into the data analysis processing part 7.

The data analysis processing part 7 detects phase shift $\angle\beta(t+\Delta T/2)$ during $\Delta T$ second by the detected reflected signal $y(x;t)$ from the object at time t and the detect reflected signal $y(x;t+\Delta T)$ at time $t+\Delta T$, and calculates the movement distance of the object during $\Delta T$ second. In this calculation, for suppressing noise, it obtains the phase shift $\angle\beta(t+\Delta T/2)$ during the $\Delta T$ second by using minimizing the squared difference between the signal $y(x;t)$ at time t and the signal $y(x;t+\Delta T)$ at time $t+\Delta T$ under a constraint condition that the amplitudes do not change and only the phase and reflection positions change between signals of time t and time $(t+\Delta T)$ and further calculates the vibration velocity $v(t)$.

(2-1) Method Increasing the Accuracy of Phase Deference Calculation

FIG. 2 shows a model of waveform of the detected signals of the reflected signals (complex signal), and signal $y(x;t)$ at time t is shown in figure (*a*), and the next signal $y(x;t+\Delta T)$ is shown in figure (*b*). The mark of □ shows real component and mark of X shows imaginary component.

When the object moves $\delta x$ after $\Delta T$ second for the detected signal $y(x;t)$, an error $\alpha(\Delta\theta(\delta x);\delta x)$ between the detected signals $y(x;t)$ and $y(x+\delta x,t+\Delta T)$ under the constraint that amplitude does not change and only phase of $\Delta\theta(\delta x)$ change is denoted as a following equation $$\alpha(\Delta\theta(\delta_x); \delta_x) = \frac{\sum_{x \in R} |y(x + \delta_x; t + \Delta T) - \exp\{j\Delta\theta(\delta_x)\}y(x; t)|^2}{\sum_{x \in R} \{|y(x + \delta_x; t + \Delta T)|^2 + |y(x; t)|^2\}/2} \quad (1)$$

where $x \in R$ means that the sum is calculated for x in a rage R. It is necessary for finding $\delta x$ which minimizes the error $\alpha(\Delta\theta(\delta x); \delta x)$. It may be happen for the signal power in the range R to change by the movement $\delta x$ of signal $y(x;t+\Delta t)$, therefore, for normalizing the power, the right-hand side of the equation (1) is divided by the denominator which is the average power of two signals.

FIG. 3 shows the change of the error $\alpha(\Delta\theta(\delta x);\delta x)$ for $\delta x$. A case that permits both of phase and amplitude to change is shown in FIG. 3 (*a*), and as shown from it, it takes minimum in all region for larger than true value $\delta x=-5$. The other case that permits only phase to change is shown in FIG. 3(*b*), as shown in (*b*), only one minimum value can be obtained at true value $\delta x=-5$.

For obtaining $\Delta\theta(\delta x)$ which minimizes the equation (1) for $\delta x$, taking account of a partial differential equation of $\alpha(\Delta\theta(\delta x);\delta x)$ by $\Delta\theta(\delta x)$ and making the equation equal to zero, by resolving the equation the suitable $\Delta\theta(\delta x)$ minimizing $\alpha(\Delta\theta(\delta x);\delta x)$ is obtained as following.

$$\exp\{j\Delta\theta(\delta x)\} = \exp(j\angle C(\delta x)) \quad (2)$$

where $C(\delta x)$ is following $$C(\delta x) = \sum_{x|R} y^*(x;t) \cdot y(x+\delta x; t+\Delta T) \quad (3)$$

And $\angle C(\delta x)$ is phase of complex number $C(\delta x)$. Mark "*" shows conjugate complex. And further, changing $\delta x$ in a range, the above equation is calculated for each $\delta x$. From the results, $\delta x$ and $\Delta\theta(\delta x)$ which make the error minimum are obtained. By using such obtained $\Delta\theta(\delta x)$, an average velocity $\hat{v}(t+\Delta T/2)$ in this range can be calculated with following equation.

$$\hat{v}\left(t + \frac{\Delta T}{2}\right) = -c_0 \frac{\Delta\hat{\theta}(\hat{\delta}_x)}{2\omega_0 \Delta T} \quad (4)$$

Where $\Delta T$ is a pulse transmission interval, $\omega_0=2\pi f_0$ is angle frequency of ultrasound the ultrasonic wave and $c_0$ is propagation velocity of the ultrasound.

(2—2) Method of Increasing the Tracking Accuracy

Moreover the object displacement $\Delta\hat{x}(t+\Delta T/2)$ during $\Delta T$ is obtained multiplying to $\hat{v}(t+\Delta T/2)$ by $\Delta T$.

$$\Delta\hat{x}(t+\Delta T/2) = \hat{v}(t+\Delta T/2) \times \Delta T \quad (5)$$

The object position of the next time can be estimated by adding the displacement $\Delta\hat{x}(t+\Delta T/2)$ to the object position $x(t)$ of the former time t.

$$x(t+\Delta T/2) = x(t) + \hat{x}(t+\Delta T/2) \quad (6)$$

The tracking trace $x(t)$ can be obtained from this.

When velocity is 0.01 m/s, $\Delta T=250$ $\mu$s, the displacement is 2.5 $\mu$m. The spatial resolution is made better more than several times than that of prior art, and it is apparent from comparing zero-cross point method based on PLL shown in FIG. 4(A) with the method of this invention shown in FIG. 4(B).

FIG. 5 is a drawing of explanation of a measuring accuracy and a measuring limit of velocity measurement of reflection waves based on a prior art method shown in FIG. 4(A) and the present invention method shown in FIG. 4(B). It is apparent that the spatial resolution is $1/fclk \times c0/2$ and quantization error is large in case of the prior art method based on PLL which detects the displacement of object during $\Delta T$ with a circuit of inner clock fclk.

(2-3) Merits of the Present Invention

The small vibration in myocardium can be obtained by the present invention, and the present invention has an excellent features as followings, (a) The small vibration of myocardium of a high frequency until several hundreds Hz can be measured with a sufficient reproducibility.

(b) A local elasticity of width of 1–2 mm in myocardium and arterial wall can be evaluated noninvasively.

(c) Signal components can be obtained at any timing of one cardiac cycle.

(d) Frequency spectrum analysis is applicable.

BRIEF DESCRIPTION OF THE DRAWINGS

FIG. 4 shows an illustration explaining theoretical limitations in the estimation if the velocity of an object by (A) the previous PLL-based method and (B) the method proposed in this invention

EXPLANATION OF PREFERRED EMBODIMENT

Figure 1:
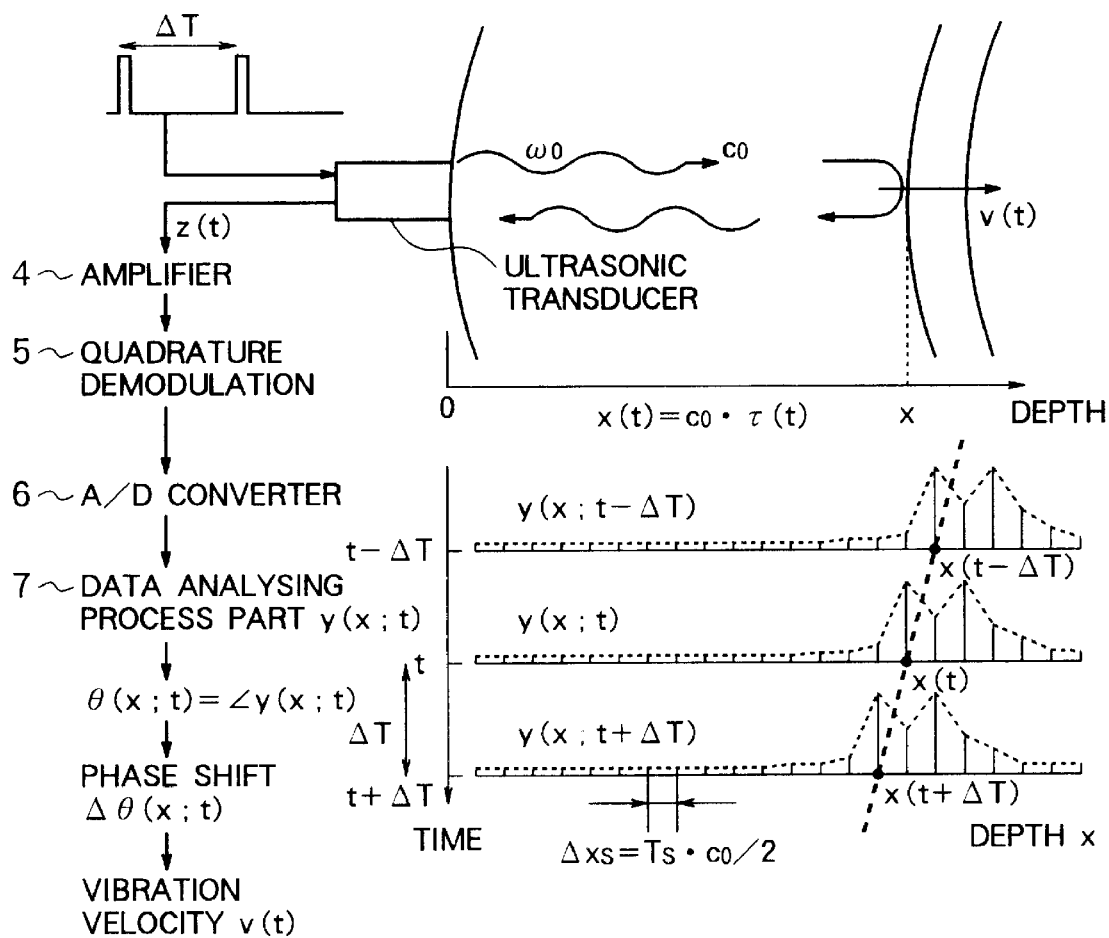
FIG. 1 shows a schematic representation of principle of the present invention.
Figure 2:
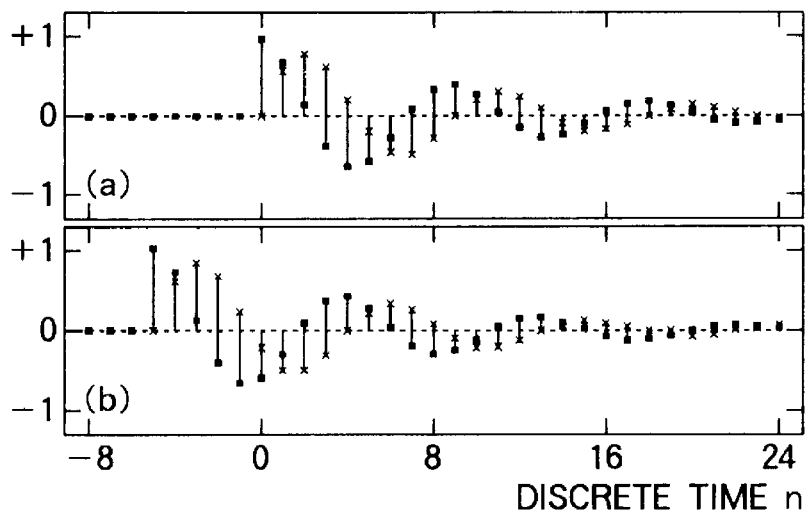
FIG. 2 is shows waveforms of a simple model of the received complex signals.
Figure 3:
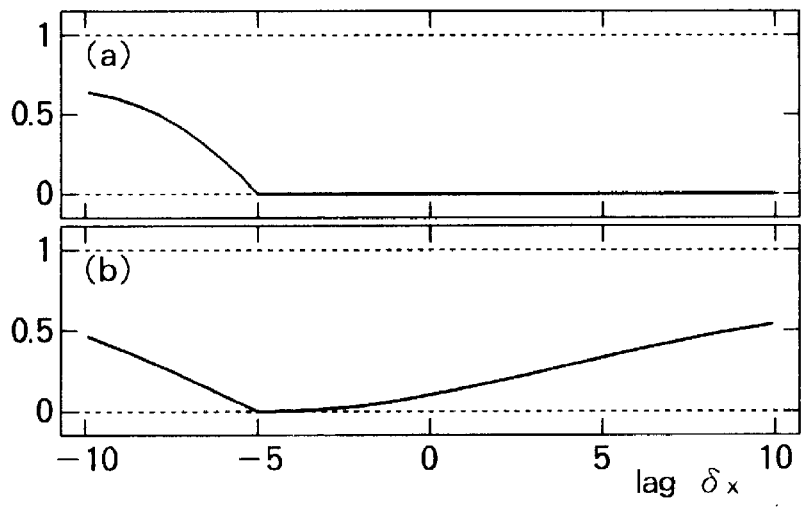
FIG. 3 shows a graph showing change of the error $\alpha(\Delta\theta(\delta x);\delta x)$
Figure 5:
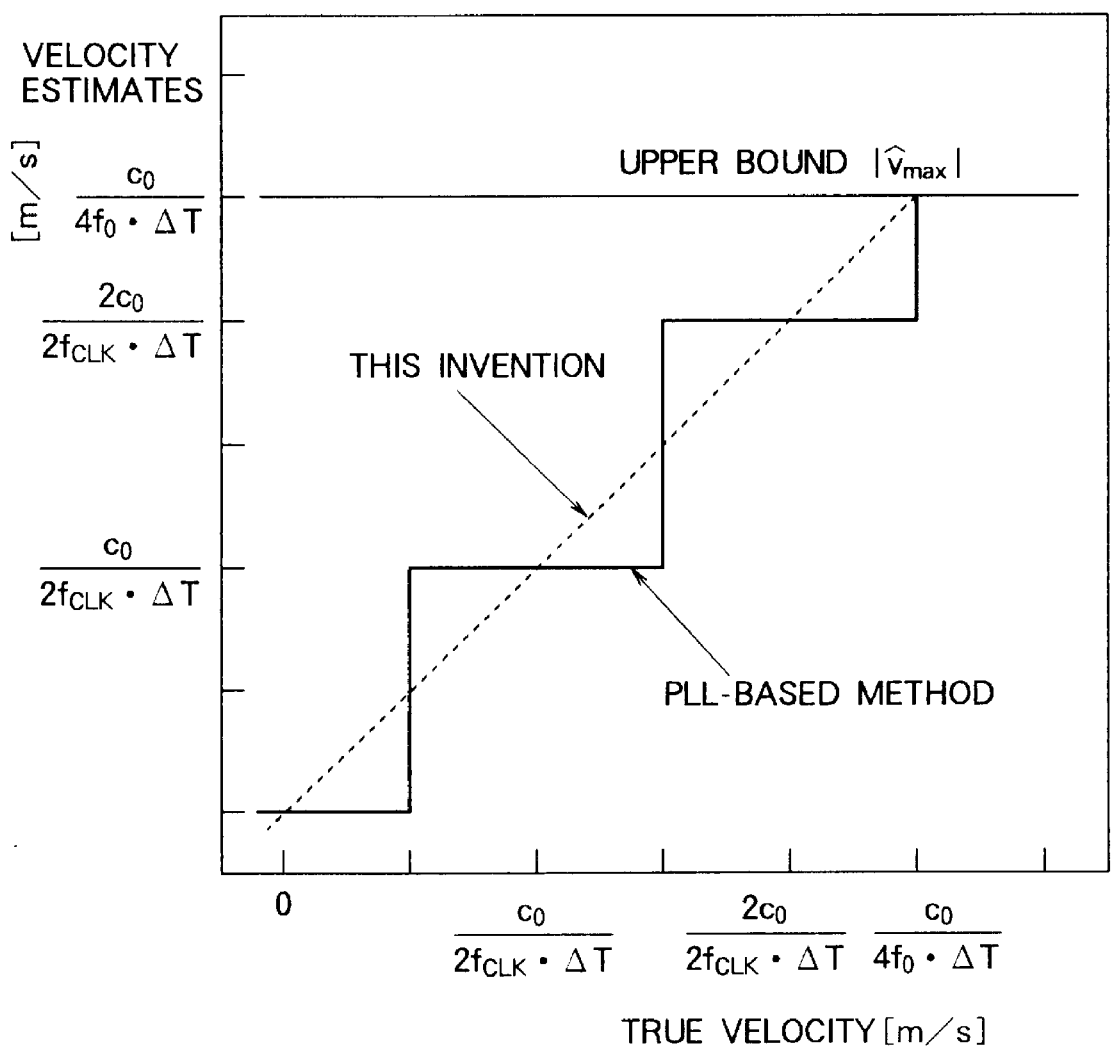
FIG. 5 shows theoretical comparison of error and the limitation in the estimation of the velocity of an object by the previous PLL-based method and the method proposed in this invention.

By this invention, quite new information for finding a myocardial infarction part and range, a quantitative diagnostic information on these degrees, can be observed with a real-time non-invasive observation from a body surface. Therefore the study on the measurement of myocardial small vibration and analysis developed by inventors of the present invention will be a pioneer in this region, and it will be a new learning region and replaced with many prior art on electrocardiogram and phonocardiogram. Further it has a possibility of application to organs like a liver and histological diagnostics of arterial wall in combination with applying a external forced vibration, for example by using a mechanical vibrator. Therefore the contribution of the present invention for non-invasive histological examination is very great.

The end-diastolic period pressure is an important factor of diagnostics for heart diseases, and there was only an invasive observation method like cardiac catheter method. As an example of application of the small vibrations of myocardial wall observed non-invasively by using this invention for the diagnostics, inventors of the present invention have proposed an epoch-making method which is possible to measure the end-diastolic pressure non-invasively by deciding eigenfrequency of the object obtained from a detailed spectrum analysis. The propriety of this invention method is confirmed experimentally, and it is a great important result in a domain of medical engineering.

Moreover a simultaneous measurement and analysis of the small vibrations of two points at distance of a few milli-meter on arterial wall is possible by using the above mentioned method. And by calculating the delay time of the pressure wave propagating on the vessel wall, the state of arterial wall can be evaluated non-invasively. These will be an effective method for diagnostics for an early stage of arterial sclerosis.

Therefore these diagnostic methods developed by inventors of this invention are original in both domains of engineering and medical science, and they are hoped a great development in near future. Further they are possible to diagnose an early stage of myocardial infarction of which patients are increasing rapidly, for reasons of it, The proposed ultrasonic diagnostic equipment will contribute to prevent and overcome it. Therefore this invention has a great social significance.

(3-1) Measurement of Myocardial Vibration and Macro Analysis of Cardiac Functions Subjects are three normal males in their twenties years old and three patients in their twenties years old who are prescribed anticancer drugs of anthracyclines series. The anthracyclines series anticancer drugs has the strongest anticancer action and have a high complete remission. For this reason, they are used frequently, but they have a nature causing a myocardial damage, and in case prescribing more than a fixed quantity of dosage it causes an irreversible cardiac insufficiency. Therefore, it is necessary to hold an exact information whether the myocardial damage is caused or not. Thus it is desired to develop an easy method to possible to diagnose it and hold its degree from the start of prescription. In this specification, it is discussed and confirmed that the myocardial damage caused by the prescription on anticancer drugs can be detected from the small vibrations of ventricular wall by using the present invention.

Figure 6:
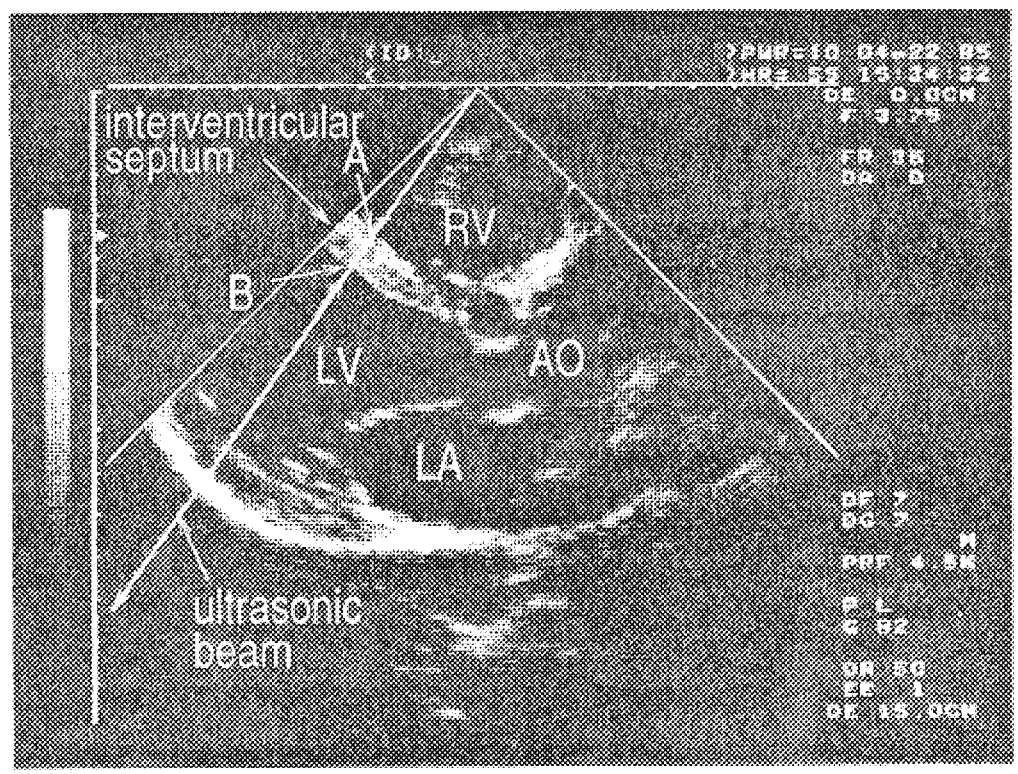
FIG. 6 shows a standard B-Mode cross-sectional image.

FIG. 6 shows a standard B-mode cross-sectional image of the male patient of 23 years old having myocardial damage. In FIG. 6, ultrasonic cross-sectional images of the right ventricular side (A point) of interventricular septum (RV) and the left ventricular side (B point) of interventricular septum (LV) are shown under a condition that the ultrasonic beam is almost perpendicular to the septum.

Figure 7:
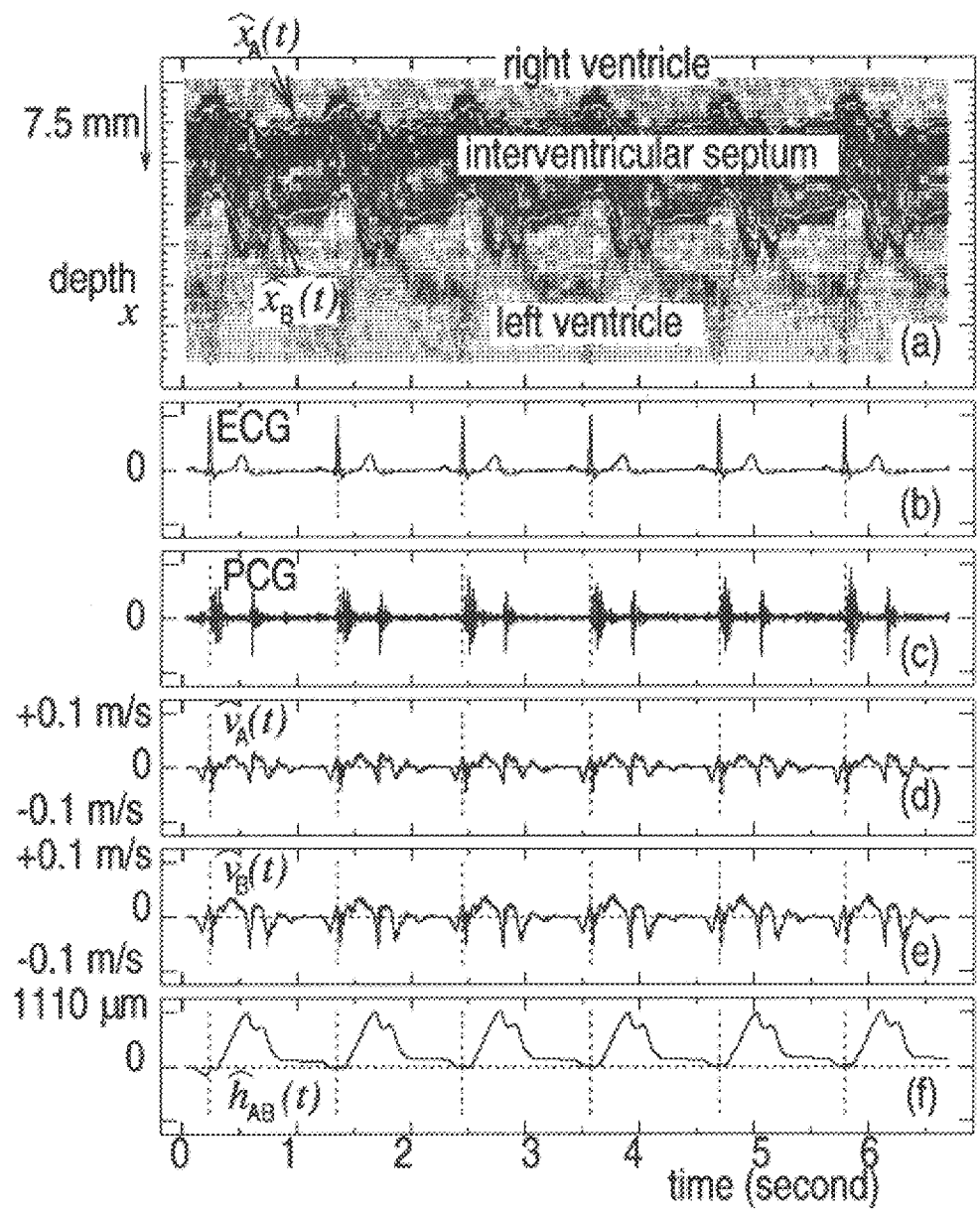
FIG. 7 shows the waveforms of movement velocity of interventricular septum.
Figure 8:
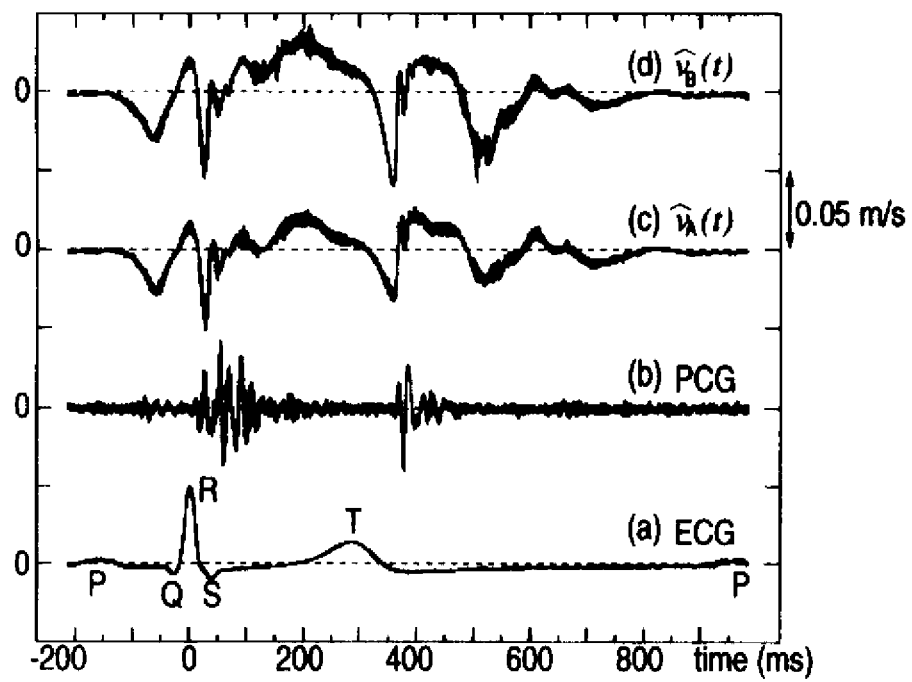
FIG. 8 shows an magnified waveform of movement velocity of interventricular septum.

FIG. 7 and FIG. 8 show vibration waveforms $v_A(t)$, $v_B(t)$, an electrocardiogram (ECG), a phonocardiogram (PCG) sound chart of the right ventricular side (A point) of interventricular septum and the left ventricular side (B point) of interventricular septum. In each figure, the ultrasonic wave is almost perpendicular to the septum. FIG. 7 (a) shows M mode, wherein a result of tracking $\hat{x}_A(t)$ and $\hat{x}_B(t)$ are overlaid, FIG. 7 (b) shows electrocardiogram, FIG. 7 (c) shows a phonocardiogram (PCG), FIGS. 7 (d), (e) show the velocity waveform $\hat{v}_A(t)$ of the right ventricular side (A point) of interventricular septum and the velocity waveform $\hat{v}_B(t)$ of the left ventricular side (B point) of interventricular septum. FIG. 7 (f) shows change of the septum thickness $\hat{h}_{AB}(t)$.

And FIG. 8(a) shows an electrocardiogram (ECG), FIG. 8 (b) shows a phonocardiogram (PCG), FIGS. 8 (c), (d) show the velocity wave $\hat{v}_A(t)$ of the right ventricular side (A point) of interventricular septum and velocity wave $\hat{v}_B(t)$ of the left ventricular side (B point) of interventricular septum.

Those for five heartbeats corresponding to R wave of the electrocardiogram are displayed.

Figure 9:
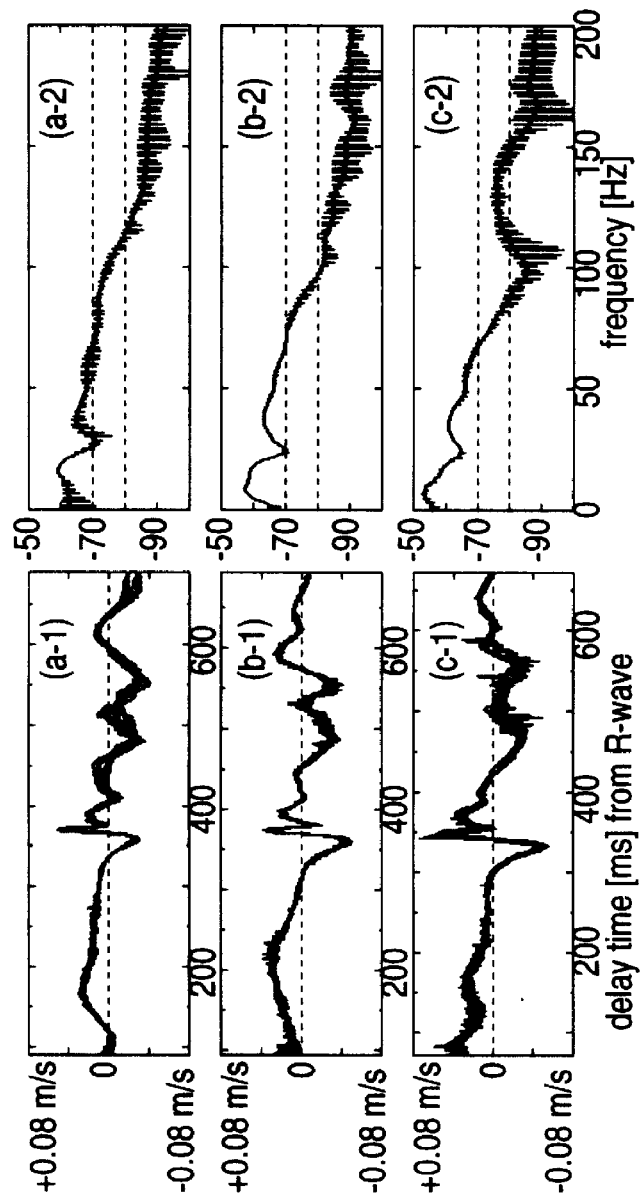
FIG. 9 shows the waveform of the vibration signals on the LV side of the interventricular septum of healthy subject (left) and their power spectra (right).
Figure 10:
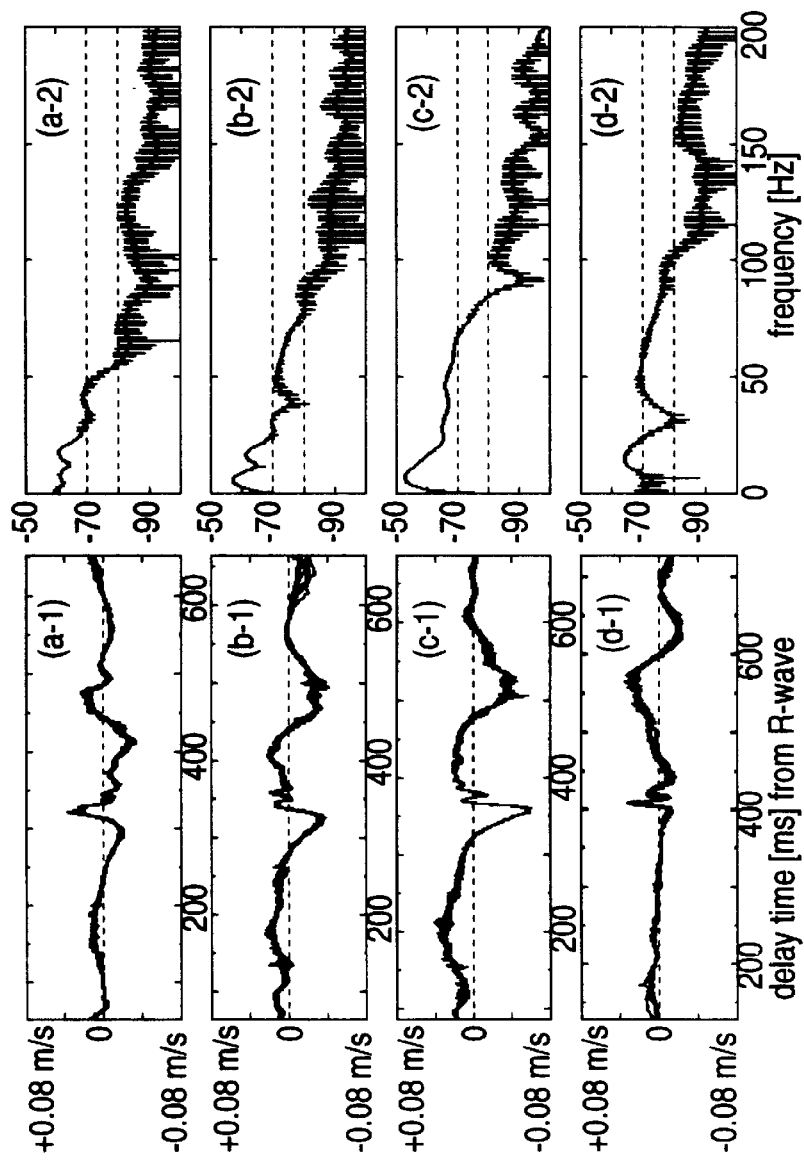
FIG. 10 shows the waveforms of the small vibration signal on the LV side of the interventricular septum for patients with myocardial disease (left) and their power spectrum (right).

FIG. 9 and FIG. 10 show velocity waveform on a surface of the left ventricular side of interventricular septum of the six subjects at timings of end ejection period— isovolumic relaxation period—rapid filling period centered to the second sound, and their mean power spectra.

In the left side of FIG. 9, waves around the second heart sound of the small vibrations of the left ventricular side of interventricular septum of three normal males of their twenties years old for several heartbeat. At the right side of FIG. 9, the average power spectrum of velocity waveform are shown. Vertical bars (showing power spectrum) show a range between the maximum and minimum power during several heartbeats. The reproducibility is quantitatively confirmed up to 100 Hz.

In the left side of FIG. 10, waveforms around the second heart sound of the small vibrations of the left ventricular side of interventricular septum of three patients having myocardial disease are overlaid for a few heartbeats and in the right side of the FIG. 10, the average power spectrum of each velocity signal is shown. Those for 8 heartbeats of the male of 32 years old measured two months before his dead are shown in the figure (*a*-1,*a*-2). Those for 8 heartbeats of same patient with FIG. 8 (*a*-1,*a*-2) measured three months before the measurement of FIG. 10 (*a*-1,*a*-2) are shown in FIG. 10 (*b*-1,*b*-2). And in figure (*c*-1,*c*-2) those for 5 heartbeats of the male of 23 years old are shown and in FIG. 10(*d*-1,*d*-2) those for 6 heartbeats of females of 25 years old are shown.

As shown in FIG. 9, the waveform of normal subjects are similar and the power spectrum distribution is also mutually similar. In contrast to these, the amplitude of the patients are clearly small as shown in FIG. 10, and all power spectra, especially up to the 100 Hz, are decreased a few ~10 dB. It is considered that the decrease of the power is caused by the decrease of myocardial functions.

Figure 11:
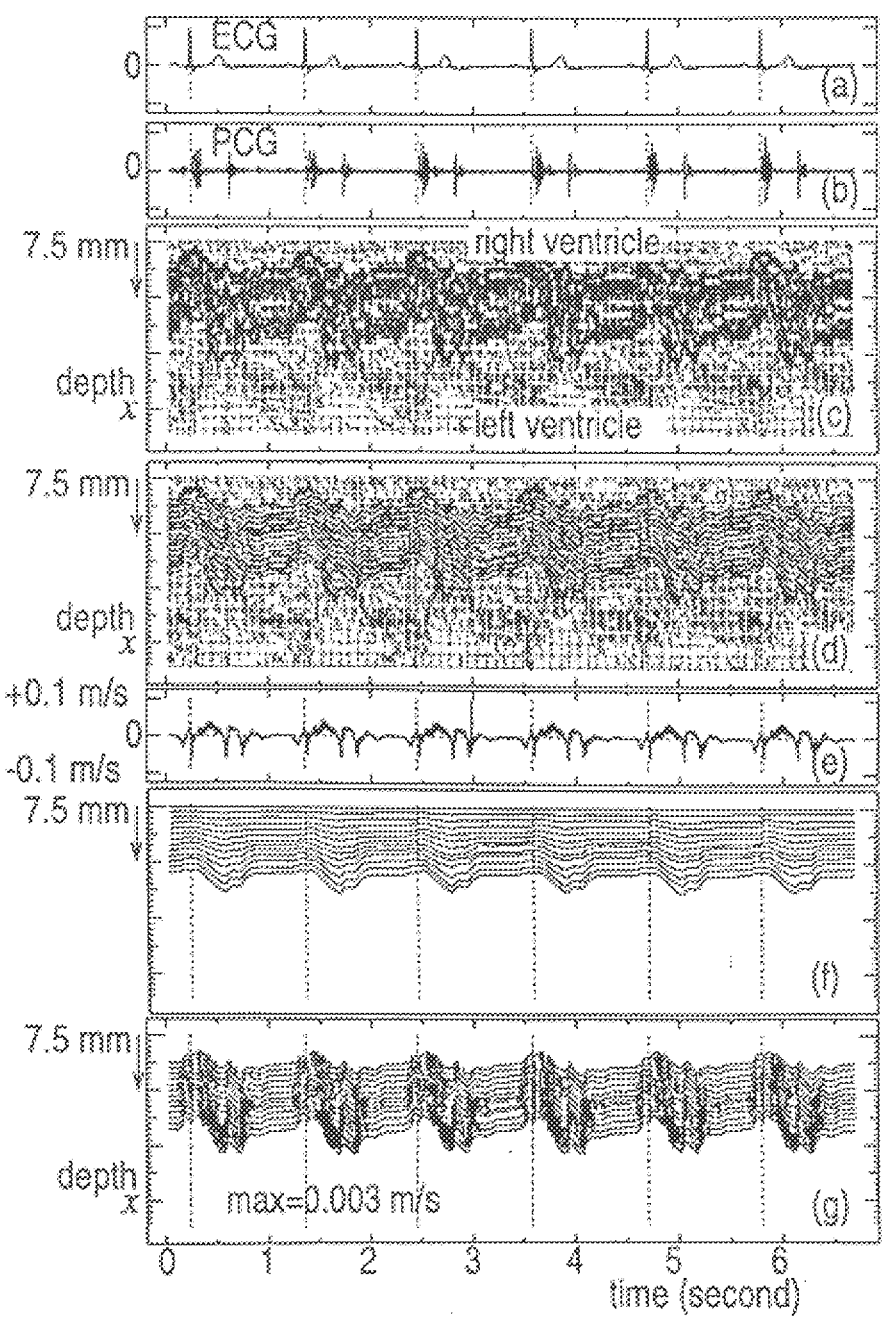
FIG. 11 shows the waveforms showing change of regional myocardial thickness at interventricular septum.

(3-2) Measurement of Change of Myocardial Thickness and Macro Analysis of Myocardial Functions Measurement results of the change of local myocardial thickness at myocardial interventricular septum are shown in FIG. 11. In FIG. 11, an electrocardiogram (ECG) is shown in figure (*a*), a phonocardiogram (PCG) is shown in figure (*b*), M-mode image is shown in figure (*c*), M mode chart and tracking results $\hat{x}i(t)$, i={1, 2, . . . , 13} of at interval of about 0.75 mm are overlaid in figure (*d*), the movement velocity signals $\hat{v}i(t)$ on each tracking trajectory are shown in figure (*e*), the waveforms of change in local thickness of the interventricular septum $\hat{x}i(t)-\hat{x}1(t)$, i={1, 2, . . . , 13} calculated from the diference between $\hat{x}i(t)$ and the tracking $\hat{x}1(t)$ at right ventriculer side are shown in figure (*f*). The absolute value of the spatial difference $|\hat{v}i+1(t)-\hat{v}i(t)|$ between the movement velocities for the result of tracking (*d*) $\hat{x}1(t)$ are shown in figure (*g*) in which the value is indicated by shading. In such a way, the change in thickness caused in each regional myocardium can be estimated.

Figure 12:
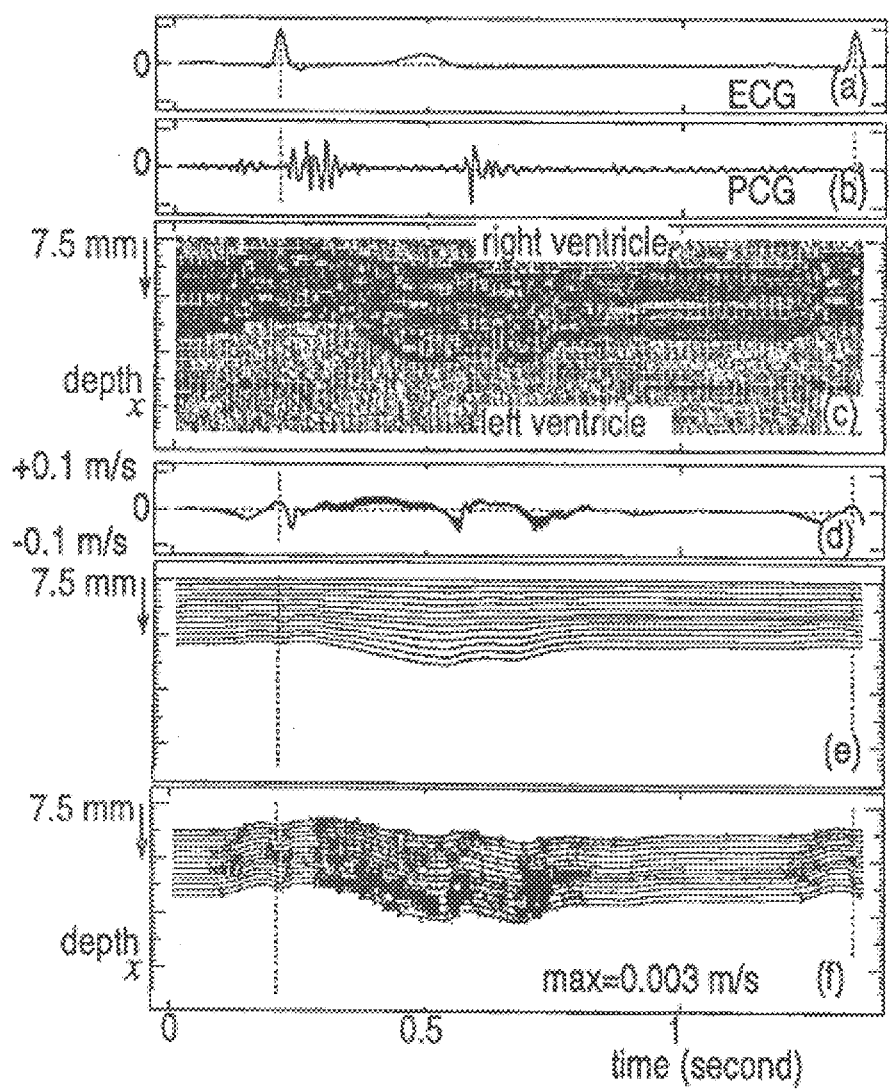
FIG. 12 shows an magnified waveform showing change of regional myocardial thickness at interventricular septum.

FIG. 12 shows a magnified of measurement result of the change in thickness of the local myocardium of interventricular septum in FIG. 11, and it shows that of one heartbeat.

In FIG. 12, an electrocardiogram (ECG) is shown in figure (*a*), a phonocardiogram (PCG) is shown in figure (*b*), M-mode image is shown in figure (*c*), the movement velocity $\hat{v}(t)$ on each tracking trajectory $\hat{x}i(t)$ is shown, the change in thickness caused in each regional myocardium of the interventricular septum $\hat{x}i(t)-\hat{x}1(t)$ calculated by the difference between the tracking result $\hat{x}i(t)$ and $\hat{x}1(t)$ at the right ventricular side is shown in figure (*e*), the absolute value of the difference of the movement velocity for tracking results $|\hat{v}i+1(t)-\hat{v}i(t)|$ in figure (*g*) is shown in figure (*f*) in which the value is indicated by shading.

(3—3) Estimation of Kinetic Energy Consumed at each Regional Myocardium

Figure 13:
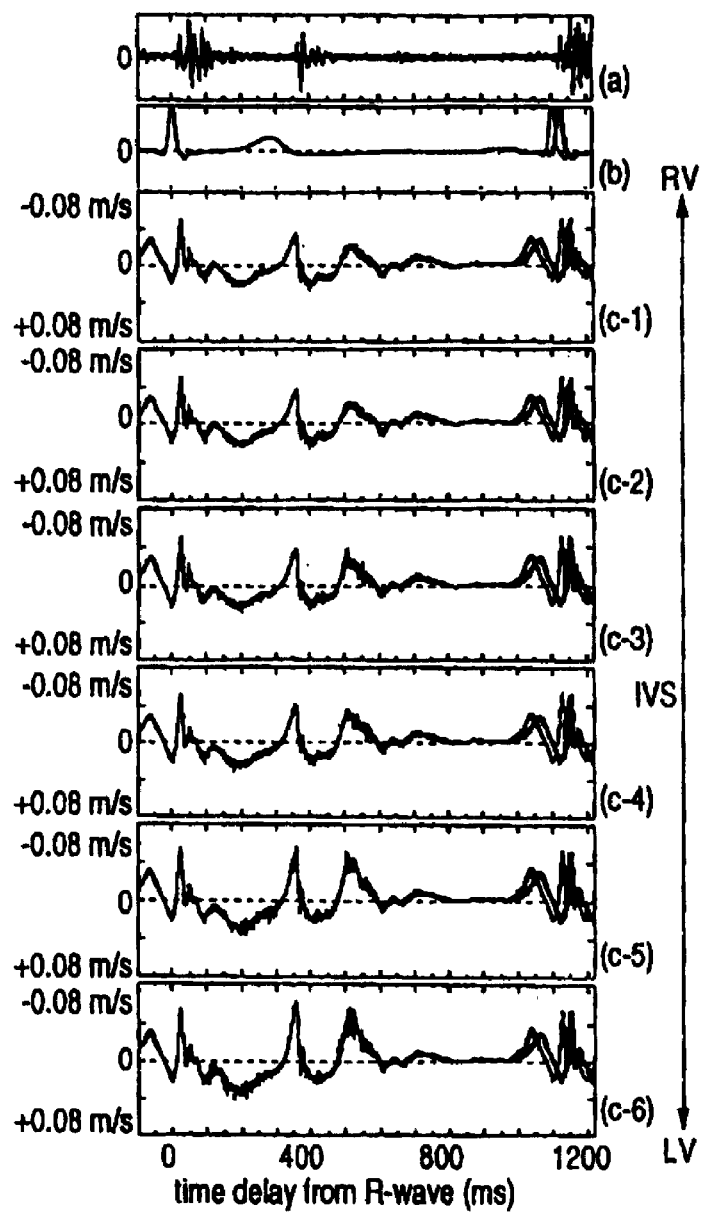
FIG. 13 shows the waveform movement velocity of interventricular septum.

In FIG. 13, the movement velocity waveforms of interventricular septum of myocardium of R wave of electrocardiogram for 5 heartbeats are overlaid. In FIG. 13, a phonocardialgram is shown in figure (*a*), an electrocadiogram is shown in figure (*b*), movement velocity waves $\hat{v}i(t)$ on each tracking trajectory $\hat{x}i(t)$, i={1, 3, 5, 7, 9, 11} same with FIG. 11 (*d*) is shown again in FIG. 13 (*c*). These trackings are measured at intervals of about 1.5 mm. The velocity waveform showing the change in myocardial thickness can be obtained by the spatial difference of these movement velocity waves $\hat{v}i(t)-\hat{v}i+1(t)$. A kinetic energy of myocardium can be calculated by multiplying the myocardial density or mass of the objective region by the square of the velocity and dividing them by two. They are corresponding to the chemical energy of oxygen and nourishment sent to the myocardial tissue from coronary arteries. Therefore, the non-invasive histological estimation of myocardial activity can be possible by this kinetic energy.

Figure 14:
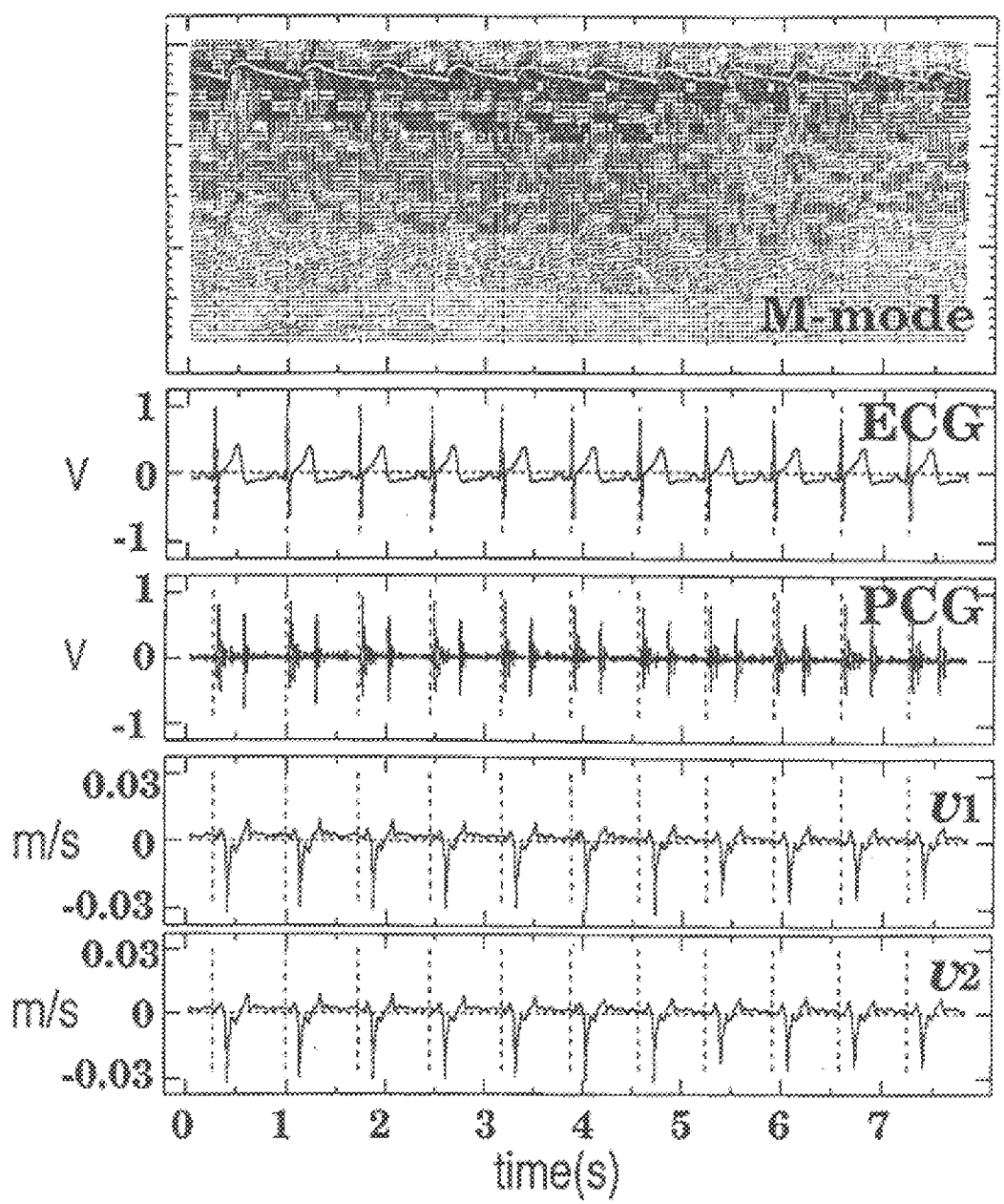
FIG. 14 shows the waveforms showing the velocity of small vibration at two points on abdominal aorta.

(4) Measurement of Change of Arterial Wall Thickness and Non-Invasive Measurement of Elasticity of Arterial Radial Direction The movement velocity wave of arterial wall can be also measured more precisely than by prior art. FIG. 14 shows calculated small vibration velocities v1,v2 at two points on wall of the abdominal aorta of a healthy male of 22 years old. The thickness changes h(t) can be obtained by calculating the difference between v1(t) and v2(t) of two waves and integrating regarding to time.

Figure 15:
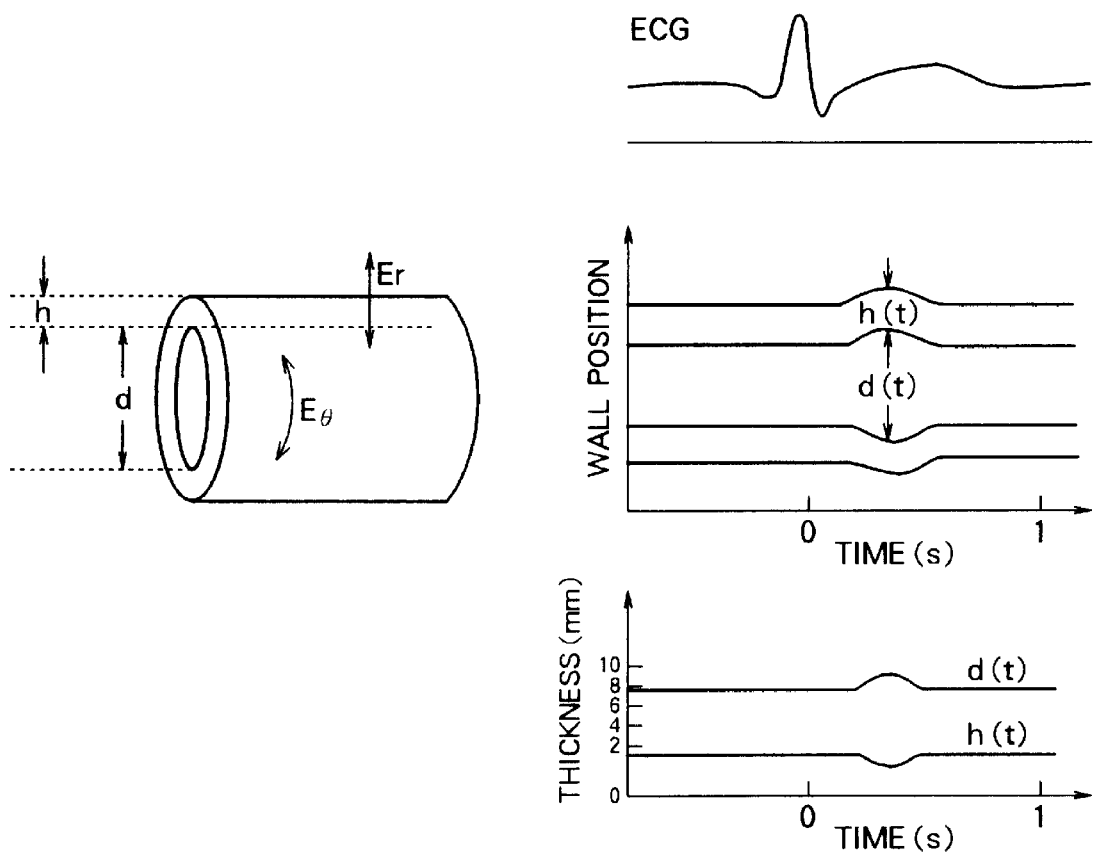
FIG. 15 shows explanation drawing of change of arterial wall thickness by a heartbeat motion.

Further as shown in FIG. 15, by combination of the change of arterial wall thickness h(t) with intraventricular pressure p(t) measured with a blood pressure meter, the modulus of elasticity of radial direction of arterial wall can be calculated. By the time change of vessel lumen d(t) and the wall thickness h(t) at one heartbeat, young's modulus Er of radial direction may be calculated as following.

distortion rate;

$$\epsilon=\Delta h/h \quad (7)$$

$$\text{Young's modulus } Er=p(t)/\epsilon \quad (8)$$

(p: intraventricular pressure)

This is a new index for diagnosing arterial sclerosis which is different from an index E θ of prior art.

(5) Non-Invasive Measurement of Intraventricular Pressure by Analyzing the Cardiac Vibration The intraventrcular pressure is a very important measure of heart diagnostic. Especially the end-diagnostic period pressure of left ventricle is necessary and indispensable for the estimation and observation of cardiac functions, but it is normally 10–20 mmHg, therefore it can not be measured at the artery of upper arm. Therefore, a cardiac catheter is used for the measurement of the end-diastolic period pressure, namely, a part of arterial of upper arm or under limb is cut open and a small pressure sensor is inserted to the ventricle through the artery for measuring the pressure. This method can measure a precise intraventricular pressure, but for the reason of an invasive observation, it cannot be executed easily and repeatedly at a place like an outpatient hospital or a bed side.

Therefore, the present invention proposes a new method for the measurement of small vibration of myocardial. It is a non-invasive observation method that observes the small vibration of myocardial wall and is possible to decide the eigenfrequency of ventricle by analyzing the spectrum of the small vibration, and further by combination with a geographical measurement of myocardial wall thickness and radius etc. decides the end-diastolic period pressure of left ventricle non-invasively. It has been resulted by a quantitative estimation based on an application of in vitro experimental data to be possible to measure the end-diastolic period pressure of left ventricle non-invasively within error of 2–3 mmHg. It is not too much to say that it is a great epoch making result on domains of medical engineering, acoustic engineering and circulatory internal medicine.

Theory of Non-Invasive Measurement of Intraventricular Pressure

According to Mirsky method for a left ventricle elasticity, when the left ventricle is supposed as an elastic shell of radius r [m] and thickness h [m], where the thickness corresponds to the ventricular wall thickness, a relation of left ventricular stiffness Eq [Pa] and the pressure p(t) [Pa] of left ventricular cavity at time t are the following.

$$Eq = 3990 \left(1 + \frac{V_w r^2}{Vr^2 + (r+h)^2}\right)\left(1 + \alpha V + \frac{\beta V}{p(t)}\right)\sigma_{m1} \quad (9)$$

Where V is the volume of left ventricular cavity, Vw is the volume of left ventricular wall and σm is the left ventricular wall stress [Pa] at the wall center of thickness direction. And α and β are the coefficients when dp(t)/dV is expressed as dp(t)/dV=αp(t)+β. Experimentally, is calculated from αV=1n(p(t)/57.32), β can be neglected.

On the other hand, Honda, Koiwa etc. of Tohoku University have shown experimentally that the myocardial elasticity E can be approximated by a following equation, when the left ventricle is supposed as an elastic shell.

$$E = 8.7 \times 10^4 r^2 f(t)^2 \quad (10)$$

where f(t) is eigenfrequency [Hz] of left ventricular mode 2. When the left ventricular radius r, the left ventricular wall thickness h, the eigenfrequency f(t) are given, the left ventricular cavity pressure p(t) can be calculated by resolving an equation that the myocardial elasticity Eq of the left ventricle denoted by formula (9) and elasticity E denoted by formula (10) are equal.

Spectrum Analysis for Deciding the Eigenfrequency

The left ventricular radius r and wall thickness necessary for calculating the left ventricular pressure p(t) at time t can be easily measured with the ultrasonic diagnostic equipment. On the other hand, because of the nonstationaryty of cardiac wall vibration, the time frequency analysis is necessary for the estimation of instantaneous eigenfrequency f(t). Therefore, in this invention, the spectrum analysis of the nonstationary cardiac wall vibration is done by using wavelet conversion.

The eigenfrequency f(t) must be decided carefully by considering the following.

(1) The time-frequency distribution obtained from the small vibration analysis on the cardiac wall with the wavelet transformation contains various frequency components beside components of mode 2 of the left ventricle.

(2) Signal analysis accuracy depends on each spectrum analysis method or an adapted window function.

Therefore, considering that the frequency range of mode 2 of the small vibration of cardiac wall is more than 20 Hz, the frequency having the largest value of (maximum) power spectrum $|T'_\Psi(t,f)|^2$ in range of 20–80 Hz in each distribution obtained at each time t is decided as an instantaneous eigenfrequency f(t) of mode 2 of cardiac wall.

Estimation of Intraventricular Pressure Measurement by In Vitro Experiment

The estimation of intraventricular pressure of the left ventricle are done by using the small vibration s(t) of back center of left ventricle of an excised and isolated heart of canine measured by acceleration meter. FIG. 1 shows the result of the estimation of intraventricular pressure.

Figure 16:
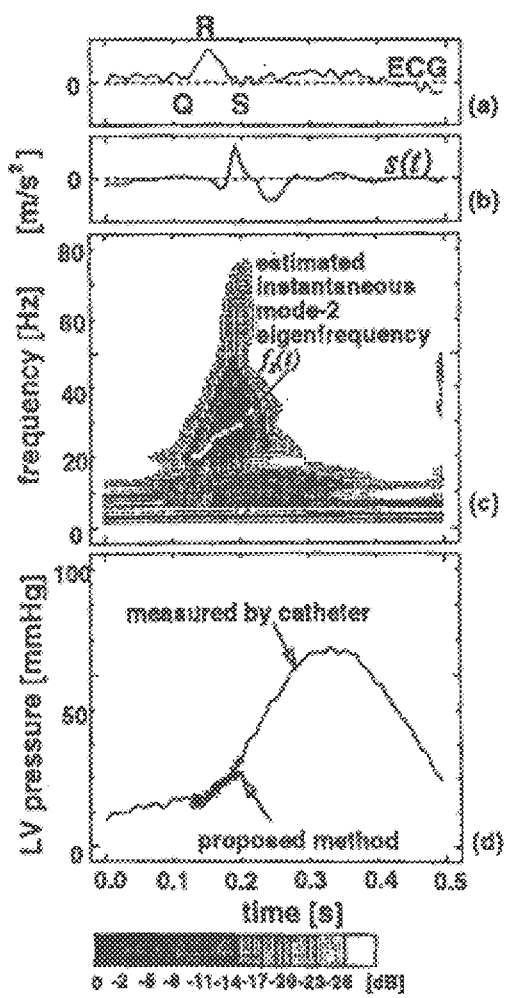
FIG. 16 shows explanation drawings of interventricular pressure estimation.

In FIG. 16, an electrocardiograph (ECG) is shown in figure (a), the cardiac vibration s(t) is shown in figure (b), the time-frequency component distribution $|T'_\Psi(ti)|^2$ is shown in figure (c) and eigenfrequency {f(ti)} is overlaid in figure (c), the intraventricular pressure p(t) of an actual measurement with catheter is shown in figure (d), in figure (d) mark of □ shows the estimated intraventricular pressure {p̂(ti)} of end-diastolic period.

The experiment for estimation is done by using Modulated Gaussian function ΨM(t), Hanning function ΨH(t), the second derivative of a Gaussian ΨSG(t) as the basic wavelet.

FIG. 16 (c) shows a time-frequency distribution $|T'_\Psi(t,f)|^2$ which is obtained by applying $\Psi_M(t)$ (m=6) to the myocardial vibration s(t) and eigenfrequency {f(ti)}(i=1, 2, . . . , 15) over 75 ms at each interval of 5 ms before 15 ms of R wave are decided.

Also FIG. 16 (d) shows an actual measurement result of the left ventricular pressure p(t) by using catheter and estimated values {p(ti)} (i=1, 2, . . . 15) around the end-diastolic period obtained by this invention.

From these consequence, the left ventricular pressure can be estimated exactly in a case of using the modulated Gaussian ΨM (t) as a basic wavelet function.

Figure 17:
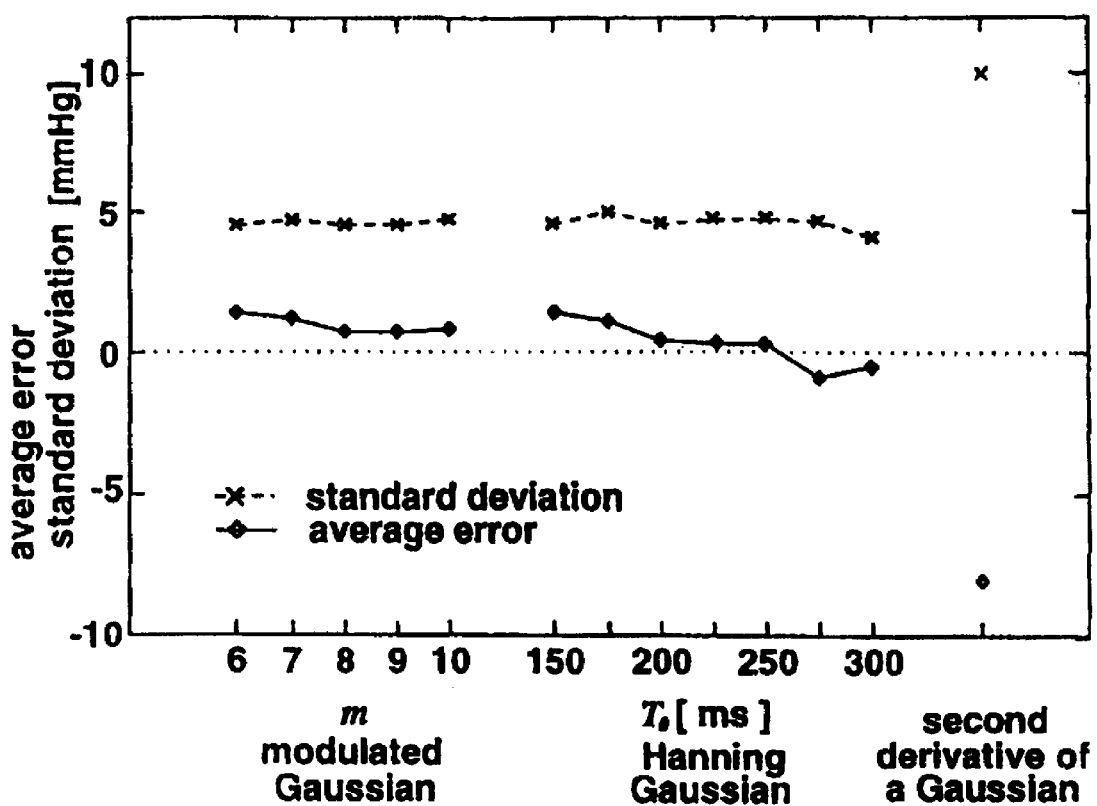
FIG. 17 shows an explanation drawing of error of invention interventricular pressure estimation at the maximum in end-diastolic period.

Furthermore, for estimating the intraventricular pressure at timing of a good S/N in end-diastolic period on eigenfrequency of mode 2, while changing the variable of the basic wavelet function, an average of Δpmax of difference between an actual measured value p(tmax) and an estimated value p̂(tmax), and a standard deviation σmax for 16 heartbeats are obtained, where the actual measured value p(tmax) at time tmax that the power of the eigenfrequwncy {f(ti)} is the maximum of 15 points in one heartbeat. The result is shown in FIG. 17. As shown in FIG. 17, both of Δpmax and σmax are very small as under a few mmHg. This shows that the intraventricular pressure of left ventricle is estimated very accurately in this invention.

What we claim is:

1. Ultrasonic diagnostic apparatus for measuring the position of an object having a vibratory motion of a large amplitude and having a small vibration which is superimposed on the large amplitude vibratory motion in a living body by transmitting an ultrasonic wave to the object, detecting a reflected ultrasonic wave from the object, and analyzing the reflected ultrasonic wave, the apparatus comprising:

a large amplitude motion analyzing means for deciding an instantaneous position of the object based on a detected amplitude and phase of the reflected wave, said large amplitude motion analyzing means tracking a reflected position of the object; and a small vibration analyzing means for measuring the small vibration of the object by calculating a changing distance of the object's position based on succeeding reflected positions of the object.

2. Ultrasonic diagnostic apparatus of claim 1, wherein:

said large amplitude motion analyzing means comprises a phase detecting means and detects a phase shift ∠β(t+ΔT/2) during ΔT by the detected reflected signal y(x;t) at a reflecting position of the object x and a time t, and by a detected reflected signal y(x;t+ΔT) at a reflected position x and at time (t+ΔT), under a constraint that an amplitude does not change and only a phase and the reflecting position change between signals of time t and time (t+ΔT), and obtains a moving distance of the object during ΔT.

3. Ultrasonic diagnostic apparatus of claim 1, wherein:

a phase detecting means and an object tracking means calculates a phase shift by a method minimizing a squared difference between signals at time t and (t+ΔT), and obtains a moving velocity of the object by the following equation, $$V\left(t + \frac{\Delta T}{2}\right) = -C_0 \frac{\beta}{2\omega_0 \Delta T}$$

where β is a phase shift ∠β(t+ΔT/2) and ΔT is a ultrasonic wave pulse transmission interval, $\omega_0$ is an angular frequency of the ultrasonic wave and $C_0$ is a propagation velocity of the ultrasonic wave, said phase detecting means and said object tracking means obtains an object displacement $\Delta \hat{x}(t+\Delta T/2)$ during $\Delta T$ by the following equation, $$\Delta \hat{x}(t+\Delta T/2) = \hat{v}(t+\Delta T/2) \times \Delta T$$

and obtains a trace of the object according to the following equation, $$x(t+\Delta T/2) = x(t) + \Delta \hat{x}(t+\Delta T/2).$$

4. Ultrasonic diagnostic apparatus of claim 1, wherein:
the object is a heart and the vibratory motion of large amplitude is a heartbeat motion, a frequency range of the small vibration is up to several hundred Hz.

5. Ultrasonic diagnostic apparatus of claim 1, wherein:
said small vibration analyzing means comprises a spectrum analyzing means and analyzes a spectrum of the small vibration.

6. A method for measuring a position of an object having a vibratory motion of a large amplitude and having a small vibration which is superimposed on the large amplitude vibratory motion in a living body, the method comprising the steps of:
transmitting an ultrasonic wave to the object;
detecting a reflected ultrasonic wave from the object;
analyzing the reflected ultrasonic wave to determine an instantaneous position of a large amplitude vibration of the object based on an amplitude and phase of the reflected ultrasonic wave;
tracking a reflecting position of the object;
measuring the small vibration by calculating a distance of the object position based on succeeding reflecting positions of the object.

7. A method in accordance with claim 6, further comprising;
detecting a phase shift $\angle \beta(t+\Delta T/2)$ during $\Delta T$ by the detected reflected signal $y(x;t)$ at a reflecting position of the object x and at time t, and from the detected reflected signal $y(x;t+\Delta T)$ at a reflecting position of the object x and at time $(t+\Delta T)$, under a constraint that an amplitude does not change and only a phase and the reflecting position change between signals of time t and time $(t+\Delta T)$;
obtaining a moving distance of the object during $\Delta T$.

8. A method in accordance with claim 6, further comprising;
calculating a phase shift between signals at time t and $(t+\Delta T)$ by minimizing a squared difference;
obtaining a moving velocity of the object by the following equation, $$V\left(t+\frac{\Delta T}{2}\right) = -C_0 \frac{\beta}{2\omega_0 \Delta T}$$

where $\beta$ is a phase shift $\angle \beta(t+\Delta T/2)$ and $\Delta T$ is a ultrasonic wave pulse transmission interval, $\omega_0$ is an angular frequency of the ultrasonic wave and $C_0$ is a propagation velocity of the ultrasonic wave;
obtaining an object displacement $\Delta \hat{x}(t+\Delta T/2)$ during $\Delta T$ by the following equation, $$\Delta \hat{x}(t+\Delta T/2) = \hat{v}(t+\Delta T/2) \times \Delta T;$$

obtaining a trace of the object according to the following equation, $$x(t+\Delta T/2) = x(t) + \Delta \hat{x}(t+\Delta T/2).$$

9. A method in accordance with claim 6, wherein:
the object is a heart and the large amplitude vibratory motion is a heartbeat motion; a frequency range of the small vibration is up to several hundred Hz.

10. A method in accordance with claim 6, further comprising;
analyzing a spectrum of the small vibration with a spectrum analyzing means.

* * * * *